United States Patent
Conca et al.

(10) Patent No.: US 7,468,341 B2
(45) Date of Patent: Dec. 23, 2008

(54) CATALYSTS FOR OXIDATION OF METHANOL TO FORMALDEHYDE

(75) Inventors: Esterino Conca, Novara (IT); Carlo Rubini, San Fermo Della Battaglia (IT); Marcello Marchi, Novara (IT)

(73) Assignee: Sud-Chemie Catalysts Italia S.R.L., Novara (IT)

( * ) Notice: Subject to any disclaimer, the term of this patent is extended or adjusted under 35 U.S.C. 154(b) by 115 days.

(21) Appl. No.: 11/303,300

(22) Filed: Dec. 16, 2005

(65) Prior Publication Data

US 2006/0135821 A1    Jun. 22, 2006

(30) Foreign Application Priority Data

Dec. 22, 2004    (IT)    ............ MI2004A2456

(51) Int. Cl.
*B01J 23/00* (2006.01)
*B01J 21/00* (2006.01)

(52) U.S. Cl. .......... 502/316; 502/255; 502/304; 502/305; 502/313; 502/314; 502/321

(58) Field of Classification Search .......... 502/304, 502/305, 313, 314, 316, 321, 255
See application file for complete search history.

(56) References Cited

U.S. PATENT DOCUMENTS

| | | | | |
|---|---|---|---|---|
| 1,913,405 | A * | 6/1933 | Meharg et al. | 568/474 |
| 2,491,695 | A * | 12/1949 | Stiles | 568/474 |
| 2,812,309 | A * | 11/1957 | Allyn et al. | 502/316 |
| 3,152,997 | A * | 10/1964 | Eugenio et al. | 502/316 |
| 3,408,309 | A * | 10/1968 | Gessner | 502/316 |
| 3,716,497 | A | 2/1973 | Courty | |
| 3,846,341 | A * | 11/1974 | Courty | 502/302 |
| 3,975,302 | A * | 8/1976 | Courty et al. | 502/263 |
| 3,983,073 | A * | 9/1976 | Trifiro et al. | 502/316 |
| 3,987,107 | A * | 10/1976 | McClellan et al. | 568/473 |
| 4,024,074 | A * | 5/1977 | Cairati et al. | 502/311 |
| 4,141,861 | A * | 2/1979 | Courty et al. | 502/302 |
| 4,181,629 | A * | 1/1980 | Cairati et al. | 502/255 |
| 4,208,353 | A * | 6/1980 | Webster et al. | 502/245 |
| 4,829,042 | A * | 5/1989 | Cavalli et al. | 502/316 |
| 5,217,936 | A * | 6/1993 | Sarup et al. | 502/241 |
| 6,331,503 | B1 * | 12/2001 | Wachs et al. | 502/305 |
| 2002/0087031 | A1 * | 7/2002 | Wachs et al. | 568/474 |
| 2003/0171624 | A1 * | 9/2003 | Wachs et al. | 568/487 |

FOREIGN PATENT DOCUMENTS

WO    WO 03/053556 A    7/2003

OTHER PUBLICATIONS

Soares A P V et al: "Iron molybdate catalysts for methanol to formaldehyde oxidation: effects of Mo excess on catalytic behaviour" Applied Catalysis A: General, Elsevier.
Soares A P V et al: "Mechanism of deactivation of Iron-molybdate catalysts prepared by coprecipitation and sol-gel techniques in methanol to formaldehyde oxidation".

* cited by examiner

*Primary Examiner*—Cam N. Nguyen
(74) *Attorney, Agent, or Firm*—Husch Blackwell Sanders LLP

(57) ABSTRACT

Catalysts for oxidation of methanol to formaldehyde, comprising a catalytic mixtures of $Fe_2(MoO_4)_3/MoO_3$, wherein the Mo/Fe atomic ratio ranges from 1.5 to 5, and a compound of cerium molybdenum and oxygen in a quantity from 0.1 to 10% by weight expressed as cerium.

10 Claims, No Drawings

CATALYSTS FOR OXIDATION OF METHANOL TO FORMALDEHYDE

BACKGROUND OF THE INVENTION

The present invention relates to a catalyst for oxidation of methanol to formaldehyde, to the method for preparing the catalyst, and to its use in processes for preparing formaldehyde.

Catalysts used industrially in processes for oxidation of methanol to formaldehyde (commonly termed iron molybdates, since $Fe_2(MoO_4)_3$ is one of the main active components), comprise both $Fe_2(MoO_4)_3$ and molybdenum trioxide ($MoO_3$), uniformly distributed within the mass of the catalyst.

In fresh catalysts, the Fe/Mo ratio is generally higher than 1.5 and not higher than 5; however, it is subject to changes during oxidation due to losses of $MoO_3$, which occur mainly at the inlet of the fresh reagents in the catalytic bed and in hot spot temperature regions (maximum temperature inside the reactor).

The loss of $MoO_3$ determines decreases in the performance of the catalyst. This requires, after a more or less long period of use, the replacement of the catalyst, which is a long and expensive operation.

The loss of $MoO_3$ causes, in addition to a reduction in the performance of the catalyst, the collapse of the catalytic bed and the consequent increase in load losses.

The need is therefore felt for a catalyst capable of providing constant performance for sufficiently long periods of time.

SUMMARY OF THE INVENTION

A catalyst has now been unexpectedly found which meets the above cited requirements and comprises, in addition to the $Fe_2(MoO_4)_3/MoO_3$ mixtures (hereinafter termed "basic catalyst"), in which the Mo/Fe atomic ratio is higher than 1.5 and does not exceed 5, also a compound of cerium, molybdenum and oxygen (hereinafter cerium molybdate) in a quantity of 0.2-10% by weight expressed as cerium. Preferably, the basic catalyst has a composition $Fe_2(MoO_4)_3$ $2MoO_3$, and cerium molybdate is present in quantities from 0.2 to 5% by weight as cerium.

The cerium molybdate is added as molybdate of cerium in which cerium can be tri- and/or tetravalent. During the activation of the catalyst and/or during use, the starting cerium molybdate can undergo transformations.

DESCRIPTION OF THE PREFERRED EMBODIMENTS

An X-ray diffractogram recorded on the finished catalyst in high-resolution conditions (using a high signal-to-noise ratio, a 40-KV copper tube, 40 microamperes, with $CuK\alpha=1.540598$ Å, range of 2 theta angle of 5 to 125, step 0.01 and collection time of 15 seconds/step) shows, at relatively low cerium concentrations (3000 ppm), diffraction lines at lattice distances d=8.44 Å, d=6.69 Å and d=4.79 Å, which do not appear in the diffractogram of the catalyst without cerium, and, at higher cerium concentrations (17000 ppm), lines which appear at shorter lattice distances and specifically at distances d=4.7 Å, d=4.29 Å, d=3.37 Å, d=3.04 Å, and d=2.75 Å, while the lines observed at concentrations of 3000 ppm shift to higher lattice distances, i.e., d=8.53 Å, d=6.74 Å and d=4.82 Å.

The addition of cerium molybdate has the effect of lowering significantly the hot spot temperature with respect to a catalyst without cerium molybdate, thus increasing the stability of the catalytic bed and therefore its life. The other catalyst performances, such as conversion of methanol and selectivity to formaldehyde, remain practically unchanged.

The catalyst is prepared starting from an aqueous suspension which contains the base catalyst, obtained according to known methods such as for example precipitation from a solution of a soluble ferric salt ($FeCl_3$, $Fe(NO_3)_3$ and similar soluble salts), mixed with a solution of a soluble molybdate, such as a molybdate of an alkaline metal and/or ammonium (suspension 1) and from a suspension of cerium molybdate (suspension 2) obtained by reacting, while hot, an aqueous mixture of molybdenum trioxide ($MoO_3$) and cerium carbonate with a cerium title of 42% by weight, with a Mo/Ce molar ratio of 1.5 to 3, preferably 1.6-2.1, until the generation of $CO_2$ ceases.

As an alternative, the suspension 2 can be obtained by mixing a suspension of a molybdate of an alkaline metal and/or of ammonium with a solution of a soluble trivalent cerium salt using a Mo/Ce ratio of 1.5 and washing with water the resulting suspension until the undesired ions ($NH_4^+$, $Na^+$ and the like) disappear.

The cerium molybdate can also be prepared and added to in the base catalyst as tetravalent cerium molybdate by reacting a cerium salt and a molybdate in an aqueous solution.

Suspensions 1 and 2 are then mixed together and the final product is dried by spray drying so as to obtain a powder suitable to form pellets, generally in the form of cylinders with a through bore or cylinders with a three-lobed cross-section, provided with through bores at the lobes, which have axes that are parallel to the axis of the granule, or having other shapes. The granules have a height of generally 2 to 7 mm.

The granules are then activated by calcination in an oxidizing atmosphere (air) at temperatures from 450° to 600° C., preferably from 480° to 580° C.

Calcination lasts generally four or more hours.

The final catalyst has a specific surface (BET) of 1-7 $m^2/g$, preferably 3-6 $m^2/g$.

It is also possible, but it is not one of the preferred methods, to mix uniformly a powder of tri- and/or tetravalent cerium molybdate with a powder or slurry of the base catalyst.

It has been found, and this is an additional aspect of the catalysts according to the present invention, that said catalysts, particularly those having a specific surface of 3-6 $m^2/g$, can be used conveniently to form the layer of the catalytic bed wherein the hot spot temperature is reached which is in contact with the fresh reagents. Use of this layer allows to reduce significantly the hot spot temperature in the catalytic bed.

The oxidation of the methanol is performed according to known methods.

The gas mixtures comprise methanol in concentrations from 6 to 10% by volume and oxygen in concentrations from 9 to 13% by volume, the remainder being inert gas (for example nitrogen).

The reactor is of the bundle-tube type and the reaction heat is removed by a cooling liquid, which circulates outside the pipes.

The linear velocity of the gases is comprised from 1 to 2 Nm/sec; the temperature of the bath is from 250 to 320° C.

Preferably, the gas mixture is fed into the reactor at a temperature comprised from 120 to 160° C.

The following examples are given to illustrate but not to limit the scope of the invention.

EXAMPLES

A pilot plant used for catalytic tests of methanol oxidation to formaldehyde is constituted by a tubular reactor immersed in a molten salt bath. The reactor is 1950 mm long and has an inside diameter of 20.4 mm. The catalyst is placed in the central part of the reactor so as to ensure maximum isothermicity.

The supply gases are introduced from the top of the reactor. The air and nitrogen are dosed by mass-flow and methanol is dosed by means of a constant-flow pump and is first sent to an evaporator.

The stream exiting the reactor and the gases after the purging column are analyzed by gas chromatography.

Example 1

Preparation of Cerium Molybdate

Reagents:
418.6 g cerium carbonate (Ce=42%)
271.0 g molybdenum trioxide

In a reactor with a capacity of approximately 10 liters, provided with efficient mechanical agitation, temperature measurement and control system, gas inlet and exit tube, the necessary demineralized water (approximately 4 liters) and the molybdenum trioxide are loaded. Heating is performed under agitation up to the temperature of 70° C.; cerium carbonate is added over approximately 60 minutes and agitation and heating are continued for approximately 5 hours. A dense and voluminous yellow precipitate is formed. The amount of the obtained cerium molybdate is sufficient to prepare approximately 58.6 kg of catalyst containing approximately 0.3% cerium.

Example 2

Preparation of Cerium Molybdate

Reagents
2.5 kg cerium carbonate (Ce=42%).
1.62 kg molybdenum trioxide

In a reactor with a capacity of approximately 20 liters, equipped with efficient mechanical agitation, temperature control and measurement system, gas inlet and exit tube, the necessary demineralized water (approximately 12 liters) is loaded together with the molybdenum trioxide. Heating is performed under agitation up to the temperature of 70° C.; cerium carbonate is added over approximately 60 minutes and agitation and heating continue for approximately 5 hours. A dense and voluminous yellow precipitate is formed. The resulting quantity of cerium molybdate is sufficient to prepare approximately 61 kg of catalyst containing approximately 1.7% cerium.

Comparison Example 1

Preparation of a Catalyst which Does not Contain Cerium

Reagents:
23.8 kg molybdenum trioxide
40.0 kg sodium molybdate dihydrate
35.2 kg ferric chloride hexahydrate In a container with a capacity of approximately 2.5 m$^3$, equipped with a mechanical agitator, a temperature measurement and control system, approximately 1 m$^3$ of demineralized water, the molybdenum trioxide and the sodium molybdate are loaded. Heating is performed to 60° C. until the solids dissolve completely.

The solution of ferric chloride, prepared separately (approximately 0.5 m$^3$), is added over 90 minutes, keeping the reaction temperature constant at 60° C.

Once the addition of the ferric chloride has ended, agitation is continued for 10 minutes, the mass is brought to the volume of 2 m$^3$ with demineralized water, agitation is stopped and cooling is allowed until room temperature is reached.

After decantation of the precipitated solid, the supernatant clear liquid is made to overflow and then the solid is filtered on a fabric filter, and washed with demineralized water to eliminate the chlorides that are present. The resulting filtration cake is poured into an appropriate tank and converted into a slurry by mechanical agitation.

The slurry is then fed to a spray-dryer, to convert it into dry powder. The resulting powder is converted, after lubrication, into pellets having the shape of a perforated cylinder. Calcination of the pellets at 500° C. for 4 hours leads to the formation of the catalyst used in the oxidation of methanol to formaldehyde.

Example 3

Preparation of a Catalyst Containing Cerium

Reagents
23.8 kg molybdenum trioxide
40.0 kg sodium molybdate dihydrate
35.2 kg ferric chloride hexahydrate In a container with a capacity of approximately 2.5 m$^3$, equipped with a mechanical agitator, and with temperature measurement and control system, approximately 1.0 m$^3$ of demineralized water, the molybdenum trioxide and the sodium molybdate are loaded. Heating is performed up to the temperature of 60° C. until the solids dissolve completely.

The solution of ferric chloride prepared separately (approximately 0.5 m$^3$) is added over a period of 90 minutes, keeping the reaction temperature constant at 60° C.

Once the addition of the ferric chloride has ended, agitation is continued for 10 minutes, the mass is brought to the volume of 2 m$^3$ with demineralized water, agitation is stopped and cooling is allowed until room temperature is reached.

After decantation of the precipitated solid, the supernatant liquid is overflowed and then the solid fraction is filtered on a fabric filter, and washed with demineralized water to eliminate the chlorides that are present. The resulting filtration cake is poured into an appropriate tank and converted into a slurry by mechanical agitation. The resulting slurry is added with the suspension of cerium molybdate prepared according to Example 1. After vigorous agitation for at least 30 minutes, the resulting suspension is fed to a spray dryer, to obtain a dry powder. The resulting powder is converted, after lubrication, into cylindrical pellets which have a three-lobed cross-section and are provided with through bores at the lobes. The calcination of the pellets at 500° C. for four hours leads to the formation of the catalyst containing 0.3% by weight of cerium (from chemical analysis), in the form of cerium molybdate.

Example 4

Preparation of a Catalyst Containing Cerium

Reagents:

23.8 kg molybdenum trioxide 40.0 kg sodium molybdate dihydrate 35.2 kg ferric chloride hexahydrate In a container with a capacity of approximately 2 m$^3$, provided with a mechanical agitator, temperature measurement and control system, approximately 1 m$^3$ of demineralized water, the molybdenum trioxide and the sodium molybdate are loaded. Heating is performed up to the temperature of 60° C., until complete dissolution of the solids is achieved with consequent formation of sodium dimolybdate.

The solution of ferric chloride prepared separately (approximately 0.5 m$^3$) is added over a period of 90 minutes, keeping the reaction temperature constant at 60° C.

Once the addition of the ferric chloride has ended, agitation is continued for 10 minutes, the mass is brought to the volume of 20 m$^3$ with demineralized water, agitation is stopped, and cooling to room temperature is allowed.

After decantation of the precipitated solid, the supernatant clear liquid is overflowed and then the solid is filtered on a fabric filter and washed with demineralized water to eliminate the chlorides that are present. The resulting filtration cake is poured into an appropriate tank and converted into a slurry by mechanical agitation.

The resulting slurry is added with the suspension of cerium molybdate prepared according to Example 2.

The two products are mixed uniformly by vigorous agitation for at least 30 minutes and then fed to a spray dryer, which allows to obtain a dry powder.

The resulting powder is converted, after lubrication, into three-lobed pellets of the type prepared in Example 3.

Calcination of the pellets at 500° C. for four hours leads to the formation of the catalyst, which contains approximately 1.56% by weight of cerium, (from chemical analysis) in the form of cerium molybdate.

Comparison Example 2

The preparation of Comparison example 1 is repeated with the only difference that together with the molybdenum trioxide and the sodium molybdate, 418.6 kg of cerium carbonate and the corresponding quantity (271 g) of molybdenum trioxide are loaded.

The cerium present in the powder after calcination is only 20% of the cerium present in the starting cerium compound.

Example 5

Catalytic Tests

A catalytic bed is used which is constituted by two layers: an upper layer of 400 mm of ceramic rings and a lower layer of 700 mm of catalyst.

The total inlet gas flow-rate is 1765 Nl/hour. The O$_2$ content of the mixture at inlet is 9.5%.

The results of the test by using the catalyst of Comparison example 1 are given in the following table:

| Hours of operation | Bath ° C. | Methanol at inlet % | Methanol conversion % | Formaldehyde yield % |
|---|---|---|---|---|
| 25 | 260 | 6.11 | 97.40 | 91.14 |
| 55 | 265 | 6.10 | 98.39 | 91.79 |
| 82 | 265 | 7.53 | 98.46 | 91.48 |
| 135 | 265 | 9.00 | 98.95 | 90.25 |
| 155 | 260 | 6.12 | 96.24 | 89.36 |

The catalyst degrades rapidly when working at 9% methanol, and therefore the test was interrupted and repeated at 6% methanol in order to evaluate the catalyst degradation.

The results of the test using the catalyst of Example 3 are given in the following table:

| Hours of operation | Bath ° C. | Methanol at inlet % | Methanol conversion % | Formaldehyde yield % |
|---|---|---|---|---|
| 49 | 265 | 6.01 | 98.79 | 92.60 |
| 80 | 265 | 7.50 | 98.58 | 92.26 |
| 122 | 265 | 7.51 | 98.57 | 92.30 |
| 482 | 270 | 9.08 | 98.41 | 91.85 |
| 674 | 275 | 10.06 | 98.66 | 91.82 |
| 723 | 280 | 7.49 | 98.75 | 92.69 |

The results of the test by using the catalyst of Example 4 are given in the following table:

| Hours of operation | Bath ° C. | Methanol at inlet % | Methanol conversion % | Formaldehyde yield % |
|---|---|---|---|---|
| 120 | 270 | 6.05 | 98.41 | 93.02 |
| 150 | 270 | 7.54 | 98.62 | 93.33 |
| 486 | 270 | 9.06 | 98.43 | 92.99 |
| 492 | 275 | 9.04 | 98.93 | 93.25 |
| 683 | 275 | 10.07 | 98.79 | 92.53 |
| 846 | 280 | 7.53 | 98.11 | 91.68 |
| 876 | 290 | 7.55 | 99.16 | 92.35 |

The disclosures in Italian Patent Application No. MI2004A002456 from which this application claims priority are incorporated herein by reference.

What is claimed is:

1. A catalyst for oxidation of methanol to formaldehyde, comprising a catalytic mixture Fe$_2$(MoO$_4$)$_3$/nMoO$_3$, wherein n is a number from 2 to 10 and wherein the Mo/Fe atomic ratio ranges from 1.5 to 5, and a compound of cerium, molybdenum and oxygen in a quantity from 0.1 to 10% by weight expressed as cerium.

2. The catalyst according to claim 1, wherein the compound of cerium, molybdenum and oxygen is present in a quantity from 0.2 to 5% by weight expressed as cerium.

3. The catalyst according to claim 1, wherein the catalytic mixture has a composition Fe$_2$(MoO$_4$)$_3$ 2 MoO$_3$.

4. The catalyst according to claim 1, wherein cerium is in the form of tri- and/or tetravalent cerium.

5. The catalyst according to claim 1, having a surface area from 1 to 7 m$^2$/g.

6. The catalyst according to claim 5, wherein the surface area is from 2 to 6 m$^2$/g.

7. The catalyst according to claim 5, wherein the surface area is from 3 to 5 m$^2$/g.

8. The catalyst according to claim 1, is in the form of cylindrical granules having a through bore or a three-lobed cross-section, provided with a through bore at the lobes and with the axes of the bores which are parallel to the axis of the granule.

9. The catalyst according to claim 8, wherein the granule has a height from 2 to 7 mm.

10. A multilayer catalytic bed, wherein a layer of the bed in contact with a mixture of reagent gases is formed by a catalyst according to claim 1 having a surface area from 3 to 6 $m^2/g$.

* * * * *